US008686802B1

(12) United States Patent
Brown et al.

(10) Patent No.: US 8,686,802 B1
(45) Date of Patent: Apr. 1, 2014

(54) BIAS VOLTAGE TUNING OF MEMS RESONATOR OPERATION POINT

(75) Inventors: Andrew Robert Brown, Northville, MI (US); John Ryan Clark, Howell, MI (US); Wan-Thai Hsu, Saline, MI (US); Graham Yorke Mostyn, Saratoga, CA (US); William Cochrane Ingle, Mountain View, CA (US)

(73) Assignee: Micrel, Incorporated, San Jose, CA (US)

( * ) Notice: Subject to any disclaimer, the term of this patent is extended or adjusted under 35 U.S.C. 154(b) by 130 days.

(21) Appl. No.: 13/351,215

(22) Filed: Jan. 16, 2012

Related U.S. Application Data

(60) Provisional application No. 61/433,252, filed on Jan. 16, 2011.

(51) Int. Cl.
*H03B 5/30* (2006.01)
*G01R 23/00* (2006.01)
*G01N 27/00* (2006.01)

(52) U.S. Cl.
USPC ............. 331/154; 331/44; 331/185; 333/186; 324/71.1

(58) Field of Classification Search
USPC ..... 331/116 R, 116 FE, 116 M, 154, 156, 44, 331/185; 333/186, 200; 324/71.1
See application file for complete search history.

(56) References Cited

U.S. PATENT DOCUMENTS

| 6,249,073 | B1 | 6/2001 | Nguyen et al. |
| 6,930,569 | B2 | 8/2005 | Hsu |
| 7,211,926 | B2 * | 5/2007 | Quevy et al. .................. 310/315 |
| 7,449,968 | B1 | 11/2008 | Cioffi |
| 2002/0069701 | A1 | 6/2002 | Hsu et al. |

OTHER PUBLICATIONS

Hsu et al., "Frequency Trimming for MEMS Resonator Oscillators", Frequency Control Symposium, 2007 Joint with the 21st European Frequency and Time Forum. IEEE International. IEEE, 2007.*

* cited by examiner

*Primary Examiner* — Ryan Johnson
(74) *Attorney, Agent, or Firm* — Lempia Summerfield & Katz LLC

(57) ABSTRACT

A method of configuring a device comprising a MEMS resonator includes initiating operation of the device, estimating a first parameter of the MEMS resonator based on the initiated operation, the first parameter not varying with the bias voltage, monitoring the operation of the device at a plurality of levels of the bias voltage, calculating a second parameter of the MEMS resonator based on the monitored operation, the second parameter varying with the bias voltage, determining an operational level of the bias voltage based on the estimated first parameter and the calculated second parameter, and configuring the device in accordance with the determined operational level of the bias voltage.

20 Claims, 16 Drawing Sheets

BIAS VOLTAGE TUNING OF MEMS RESONATOR OPERATION POINT

CROSS-REFERENCE TO RELATED APPLICATION

This application claims the benefit of U.S. provisional application entitled "Bias Voltage Trimming for MEMS Resonator Operation Point Optimization," filed Jan. 16, 2011, and assigned Ser. No. 61/433,252, the entire disclosure of which is hereby expressly incorporated by reference.

BACKGROUND OF THE DISCLOSURE

1. Field of the Disclosure

The disclosure relates generally to micromechanical devices or micro-electromechanical systems (MEMS) and, more particularly, to micromechanical or MEMS resonators.

2. Brief Description of Related Technology

MEMS resonators are attractive for use in many applications as a cost-effective replacement for discrete devices such as quartz crystal oscillators or surface-acoustic wave (SAW) resonators. MEMS resonators are particularly promising for use in integrated frequency reference and timing devices, as MEMS resonators can be fabricated alone or on substrates with other circuitry, such as MOS or bipolar circuits. MEMS resonators can also have very high mechanical quality factors (Q), which lead to good frequency selectivity.

MEMS resonators have also been used to replace quartz crystal oscillators in several clock and timing applications. Some of these applications demand excellent frequency stability across a wide range of environmental conditions. For example, certain clock and timing applications call for oscillators stable to a few to tens of parts per million (ppm) over a temperature range from about −40° C. to about 85° C. or even about −55° C. to about 125° C.

The high-Q nature of MEMS resonators and normal fabrication process variations lead to challenges in fabricating MEMS resonators with frequency accuracy better than a few percent. The resonant frequency of a MEMS resonator is determined by its physical characteristics, which are, in turn, functions of design, materials, and the processing methods used to fabricate the resonator. Due to the small size of MEMS resonators and the material properties of silicon, the frequency of a MEMS resonator is sensitive to temperature variations.

Electrostatic MEMS resonators are also sensitive to variations resulting from the manufacturing process. In electrostatically driven MEMS resonators, a bias voltage is applied to the resonator between a resonator body and a driving electrode, and an AC signal is applied to the driving electrode. Once the frequency of the AC signal equals the natural resonant frequency of the resonator, the resonator starts to vibrate at the resonant frequency. The gap between the driving electrode and the resonator body and the spring constant of the resonator body are two parameters that affect resonator operation. Each parameter is subject to manufacturing process variation.

SUMMARY OF THE DISCLOSURE

In accordance with one aspect of the disclosure, a method is useful for configuring a device including a MEMS resonator, the MEMS resonator including a resonant structure to which a bias voltage is applied. The method includes initiating operation of the device, estimating a first parameter of the MEMS resonator based on the initiated operation, the first parameter not varying with the bias voltage, monitoring the operation of the device at a plurality of levels of the bias voltage, calculating a second parameter of the MEMS resonator based on the monitored operation, the second parameter varying with the bias voltage, determining an operational level of the bias voltage based on the estimated first parameter and the calculated second parameter, and configuring the device in accordance with the determined operational level of the bias voltage.

In some embodiments, configuring the device includes storing data indicative of the operational level of the bias voltage in a memory of the device. The memory may include a one-time programmable read-only memory.

Determining the operational level of the bias voltage may be further based on a frequency model of the MEMS resonator. The frequency model of the MEMS resonator may be based on empirical data representative of the operation of the device.

Alternatively or additionally, determining the operational level of the bias voltage includes estimating the bias voltage that gives rise to an offset in resonant frequency. The offset may be about 10 parts per million (ppm).

In some embodiments, the first parameter is indicative of a thickness of the resonant structure. Alternatively or additionally, the second parameter is indicative of a gap between the resonant structure and an electrode to which an excitation voltage is applied.

In accordance with another aspect of the disclosure, a device includes a MEMS resonator having a resonant structure having a thickness and an electrode spaced from the resonant structure by a gap, and further includes a circuit coupled to the MEMS resonator and configured to control a bias voltage applied to the resonant structure and based on the gap and the thickness. The circuit includes a memory in which data indicative of the bias voltage is stored and a configuration port coupled to the memory to store the data indicative of the bias voltage.

The memory may include a configurable memory. Alternatively or additionally, the memory includes a one-time programmable read-only memory.

The circuit may include a processor coupled to the memory and configured to access the data indicative of the bias voltage and further configured to develop the bias voltage in accordance with the data. Alternatively or additionally, the circuit further includes an adjustable power supply comprising the memory.

In some embodiments, the circuit further includes an amplifier coupled to the MEMS resonator to amplify an output signal of the MEMS resonator in accordance with a gain level for sustaining vibration of the MEMS resonator, the gain level being determined by an output of the adjustable power supply. Alternatively or additionally, the circuit further includes a reference oscillator coupled to the MEMS resonator and configured to generate the excitation voltage at an amplitude determined by an output of the adjustable power supply. The circuit may alternatively or additionally include a pair of oscillator output terminals driven by the MEMS resonator.

The data indicative of the bias voltage may be reflective of a frequency deviation model of the MEMS resonator. Alternatively or additionally, the data indicative of the bias voltage is reflective of an operational point for the MEMS resonator at which the frequency deviation model indicates a frequency offset of about 10 ppm.

BRIEF DESCRIPTION OF THE DRAWING FIGURES

For a more complete understanding of the disclosure, reference should be made to the following detailed description FIG. 1 is a flow diagram of an exemplary method of configuring a MEMS resonator in accordance with one embodiment.

Figure 1:
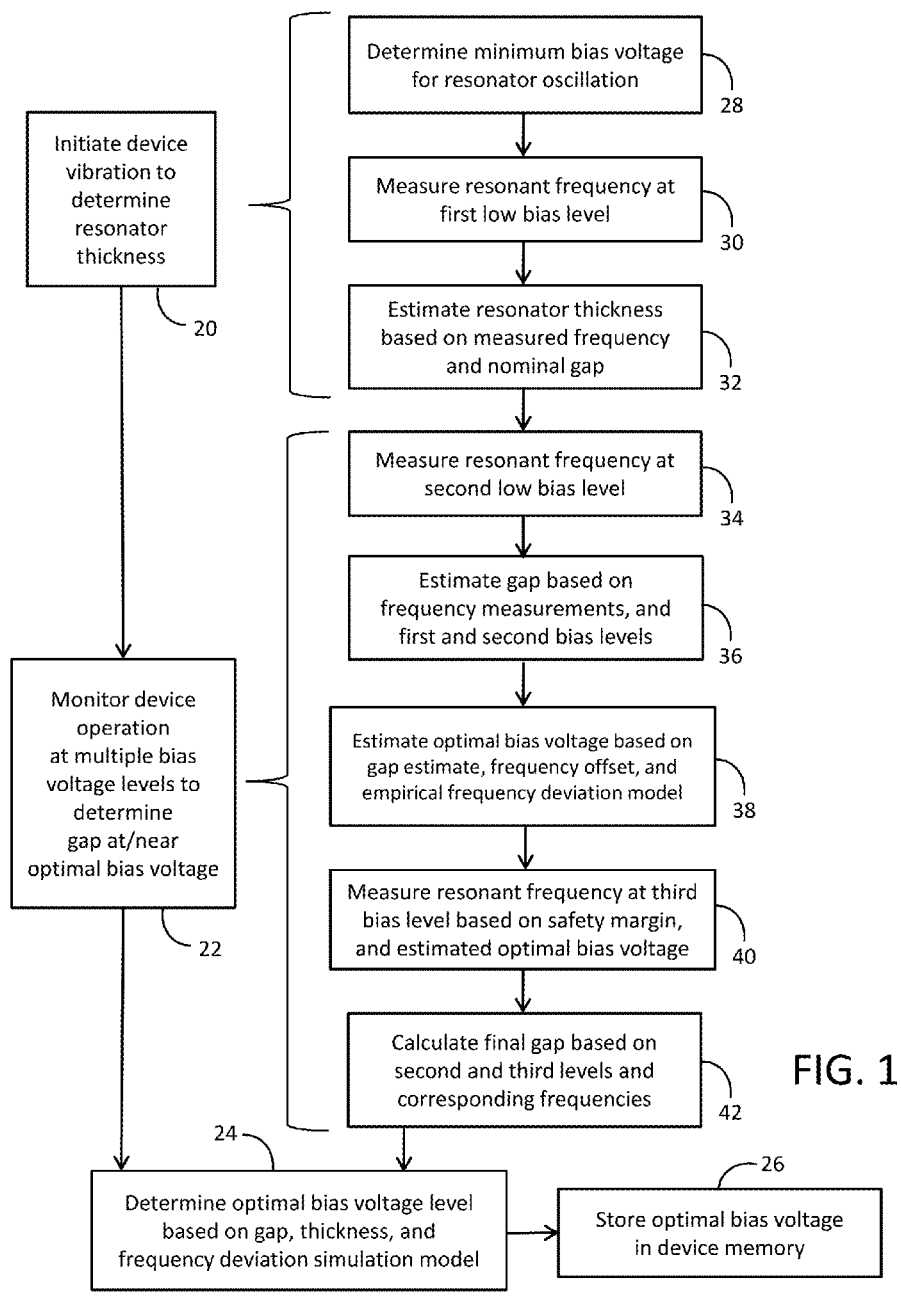

While the disclosed methods and devices are susceptible of embodiments in various forms, there are illustrated in the drawing (and will hereafter be described) specific embodiments of the invention, with the understanding that the disclosure is intended to be illustrative, and is not intended to limit the invention to the specific embodiments described and illustrated herein.

DETAILED DESCRIPTION OF THE DISCLOSURE

The invention generally relates to MEMS resonator devices and methods of configuring such devices in which a bias voltage of the device is tuned or trimmed to achieve a desired operation point for the device for improved frequency stability across variations of parameters such as gap spacing and device thickness (or spring constant). The disclosed devices and methods may thus address variance of 1-3% in such parameters due to fabrication process variations. In one aspect, the disclosed devices and methods are based on a resonator frequency model directed to configuring the resonator for operation at an optimal or desired operation point for best or improved oscillator performance (e.g., low jitter) under all operating conditions. The disclosed devices may accordingly be used in clock and timing applications calling for oscillators stable to a few to tens of ppm over the temperature ranges of interest.

One or more aspects of the disclosed methods and systems are based on one or more of the following factors or parameters of electrostatic transduction in MEMS resonators: (i) gap spacing between electrode and resonator, (ii) bias voltage across the resonator and electrode, and (iii) spring constant of the resonator. Additional or alternative factors or parameters may be incorporated or used. For a specific resonator, manufacturing process variation may not lead to significant variance in the area of the electrode(s), but the spring constant and the gap spacing may depend strongly on the process variation. The bias voltage is set to achieve optimal or desired resonator operations as well as reduce the effects of these and/or other process variations.

The method may be implemented during a configuration and/or testing phase of production in which data representative or indicative of a number of characteristics or parameters of the MEMS resonator device are extracted or obtained. The data may be indicative of any number of design characteristics or parameters, such as dimensions, that vary as a result of fabrication process irregularities. The data representative of the MEMS resonator device characteristics may be used during the configuration and/or testing phase to calibrate or configured the MEMS resonator device. For instance, the calibration may include implementing one or more procedures directed to specifying one or more operation points of the MEMS resonator device. The operation point(s) may be specified via any number of operational parameters, including, for instance, a level of a bias voltage for the MEMS resonator device. The bias voltage is applied to the resonant structure of the MEMS resonator device. For example, the bias voltage may be a DC voltage applied across or between the resonant structure and one or more electrodes (e.g., a drive electrode(s), a sense electrode(s), a drive/sense electrode(s), etc.) spaced from the resonant structure by the gap. Other operational parameters may include the amplitude of an excitation voltage applied to a drive electrode. For example, the excitation voltage may be an AC signal applied across or between the resonant structure and the drive electrode. Additional or alternative operational parameters may be specified.

The disclosed MEMS resonator devices may include circuitry configured to control the bias voltage. For example, the MEMS resonator devices may include interface circuitry configured to address deviation or variation in the resonant frequency of the MEMS resonator device resulting from the bias voltage. For example, the interface circuitry may be configured to adjust an operation point of the MEMS resonator device to compensate for process variation by tuning the bias voltage. The operation point adjustments may include basing the bias voltage on the gap and the thickness resulting from the fabrication process.

Systems for implementing the disclosed methods are also described herein. The systems may be configured in accordance with one or more models to implement the disclosed configuration methods. The model(s) for the MEMS resonator may be directed to representing the manner in which the operational point and physical characteristics of the MEMS resonator lead to variability or deviation in the resonant frequency of the MEMS resonator.

The configuration methods and systems may be applied to a variety of different electrostatically transduced resonator devices. The transducer arrangement of the disclosed MEMS resonator devices may vary. For example, the design, orientation, dimensions, arrangement, and other characteristics of the resonant structure, electrodes, and other components of the MEMS resonator devices may vary from the examples described below.

Other aspects of the resonant structures may also vary from the examples described herein, including shape and resonant mode. The disclosure is not limited to any particular shape or resonant mode. Although described below in connection with beam-shaped resonant structures, other shapes (e.g., disc, ring, cylinder, etc.) may benefit from the calibration and configuration techniques described herein. The disclosed configuration methods may be applied to a variety of different resonant modes and other resonance configurations. For example, the disclosed devices may be configured for resonant vibration involving bulk acoustic vibration (e.g., wine-glass mode or other expansion mode) as opposed to flexural movement, which also may vary between different orientations and types (e.g., lateral, vertical, wine-glass mode, etc.). The disclosed methods, devices, and systems are also not limited to any particular type of process of fabricating the MEMS resonator devices, notwithstanding any references to exemplary processes involving surface micromachining and SOI-based fabrication techniques.

FIG. 1 depicts a method of calibrating or trimming a MEMS resonator device. In this example, the method begins with initiating operation of the MEMS resonator device in act or block 20 to determine or estimate a first parameter of the MEMS resonator device. The first parameter of the MEMS resonator may be a parameter that does not vary in connection with the bias voltage level applied to the MEMS resonator, such as the thickness of the MEMS resonator. The MEMS resonator thickness may correspond with the thickness of a beam or other structure of the MEMS resonant device vibrating at a resonant frequency, referred to herein as a "resonant structure." Other dimensions of the MEMS resonator device or resonant structure thereof may also be determined or estimated. Additional device parameters that do not vary in connection with the bias voltage level may also be determined.

A second parameter or characteristic of the MEMS resonator device is calculated or determined in act 22 by monitoring the device operation at multiple operational points, i.e., multiple bias voltage levels. The second parameter differs from the first parameter(s) in the sense that the parameter varies with the bias voltage level. One such characteristic of the MEMS resonator device is the size of a gap between the resonant structure and one or more electrodes (e.g., a drive electrode(s), a sense electrode(s), a drive/sense electrode(s), etc.). The size of the gap may change as a result of the application of the bias voltage, as the resonant structure is electrostatically pulled toward the electrode(s). In one example, the gap is calculated or determined in act 22 by monitoring the operation of the MEMS resonator at or near one or more typical, optimal or otherwise representative operational conditions, including bias voltage levels. Other dimensions of the MEMS resonator device may also be determined or estimated. Additional device parameters that vary in connection with the bias voltage level may also be determined. Further details regarding the bias voltage are provided below in connection with examples of devices configured in accordance with the disclosed methods.

The nature of the first and second parameters may vary depending on, for instance, the design or configuration of the MEMS resonator device, the resonant structure of the MEMS resonator device, or other component of the MEMS resonator device. The first and second parameters or characteristics are thus not limited to dimensional characteristics. Other structural properties or characteristics of the MEMS resonator may be used as, or incorporated into, the first and/or second parameters. Non-structural properties or characteristics may also be used or incorporated, including electrical, material, or operational properties or characteristics.

The determination of the magnitude or value of the second parameter(s) is complicated by not yet knowing the bias voltage at which the MEMS resonator will be operated. For example, an excessive increase may result in nonlinear operation and erroneous parameter extraction, while an insufficient increase may result in inaccuracies due to high function sensitivity. Moreover, changes to the bias voltage level may change the size of the gap. Nonetheless, the operational conditions determined via the disclosed methods may depend on data indicative of parameters such as the gap. The examples described below provide model-based techniques for determining the gap despite not yet knowing the optimal or desired bias voltage level for the MEMS resonator device. The model-based techniques may be applied to one or more other parameters or characteristics of the MEMS resonator device that vary as a function of the bias voltage level. In these and other examples, the model-based techniques may address the multi-dimensional nature of the bias voltage level determination.

An optimal or otherwise desirable bias voltage level is determined in act 24 for the MEMS resonator device based on the first and second parameter determinations (e.g., the gap and thickness values) for the MEMS resonator device. As described herein, the determination of the bias voltage level may be based on a frequency deviation model of the MEMS resonator (see, e.g., FIG. 12), which may, in turn, be based in part or in whole on simulation data for the MEMS resonator device. For example, the frequency deviation model may be used in conjunction with a harmonic balance simulation tool. Harmonic balance simulation provides a frequency domain analysis technique for simulating the non-linearity presented by the frequency deviation model, thereby linking the mechanical and frequency domains. Any one of a number of commercially available nonlinear solver simulation tools may be used.

The device may then be configured in accordance with the determined level of the bias voltage. The operation of the MEMS resonator device is thus calibrated or trimmed via the bias voltage level, thereby addressing any process variations in the first and second parameters. For example, the calibration or trimming method may conclude with the storage of data in act 26 indicative of the optimal bias voltage level in a memory of the MEMS resonator device. The memory may include a one-time programmable read-only memory. Other non-volatile memories may be used, such as an electrically erasable programmable read-only memory (EEPROM). The construction, configuration, and other characteristics of the memory may vary. The memory may, for instance, include mechanical components (e.g., a set of switches).

FIG. 1 also depicts further details regarding exemplary procedures or methods for implementing the above-described acts of the calibration method in connection with the thickness and gap parameters. The first parameter, such as the resonator thickness (e.g., the thickness of the resonant structure), may be estimated by connecting the MEMS resonator device to a power source for operation, ramping up the bias voltage level from a low level (e.g., 0 Volts), and determining in act 28 the minimum level of the bias voltage at which the MEMS resonator device oscillates. The MEMS resonator device may be operated at room temperature during these acts. With the minimum bias voltage level for oscillation known, the MEMS resonator is then operated at a low bias voltage level (e.g., 100 mV above the minimum level) to, for instance, ensure a stable start, and the resonant frequency is measured in act 30. The resonator thickness may then be estimated in act 32 in accordance with a resonator model for the resonant frequency of the MEMS resonator device, an example of which is:

$$f = f_0\left(1 - \frac{k_e}{k_m}\right)^{1/2} = f_0\left(1 - \frac{V_p^2 \varepsilon_0 A_e}{d_0^3 k_m}\right)^{1/2} \text{ where } f_0 = 1.03\sqrt{\frac{E}{\rho}}\frac{h}{L^2} \quad (1)$$

where $f_0$ is the resonator frequency without bias, E is the Young's modulus, $\rho$ is the density of resonator material, h and L are the thickness and length of the resonator, respectively, $V_p$ is the bias voltage, and d is the gap size. The estimation may also be based on a nominal, typical, or expected average gap size (e.g., 800 Angstroms). In some cases, as in the exemplary resonator model set forth below, the resonant frequency of the MEMS resonator device is proportional to the resonator thickness (e.g., resonant structure thickness).

The second parameter, such as the size of the gap, may be calculated in the example of FIG. 1 by measuring the resonant frequency of the MEMS resonator device in act 34 at a second low bias voltage level. For example, the bias voltage level may be increased by another 100 mV from the previous low bias voltage level (i.e., to 200 mV). An initial estimate of the gap size is determined in act 36 based on the resonant frequencies measured at these two bias voltage levels using, for instance, a model of the deviation of the resonant frequency from the zero-bias frequency $f_0$ induced by the bias voltage, an example of which is described further below. For example, the resonant frequency deviation from the zero-bias frequency (f-$f_0$) is modeled as a function of resonator thickness, gap, and bias voltage. As described below, the model may be solved for the gap by subtracting two instances of the resonant frequency deviation model (one for each of the resonant frequencies measured at the two bias voltage levels) from one another, thereby cancelling out the zero-bias frequency term. The removal of the zero-bias frequency term is useful because the zero-bias frequency may not easily or directly measured.

With the initial estimate of the gap, an initial estimate of an optimal or desired bias voltage level is determined in act 38 based on one or more operational parameters and based on a resonator model that attempts to model deviation of the resonant frequency induced by the bias voltage. The operational parameter(s) may be indicative of the extent to which the operational point for the MEMS resonator will reside in a non-linear region of operation. As described further below, the resonant frequency will begin to exhibit the non-linear behavior (e.g., an offset or deviation from the theoretical resonant frequency of the above-identified model) as the amplitude of the vibration approaches the size of the gap. Large amplitude vibration may, however, be useful for various reasons, such as achieving a suitable signal-to-noise ratio. Thus, one example of an operational parameter on which the bias voltage level determination may be based is an offset, a variance, or a deviation level from the linear model. In one example, the optimal or desired bias voltage level may be determined such that the resonant frequency deviates from the theoretical, linear value by an offset of about 10 ppm. The offset may vary from 10 ppm. In some cases, an offset of less than 5 ppm may result in inadequate resonator performance (e.g., low signal strength), while an offset greater than 15 ppm may result in undesirable non-linear operation. Offsets that lie between 5 ppm and 15 ppm may be useful in determining a desired bias voltage level and, thus, operational point.

With the 10 ppm frequency offset as an exemplary parameter, a model of the frequency deviation exhibited by the MEMS resonator device may be used to estimate the optimal or desired bias voltage level. As described below, the frequency deviation model may be based in part or in whole on empirical and/or simulation data for the MEMS resonator device. Alternatively or additionally, the frequency deviation model may be based on the theoretical operation of the MEMS resonator device. The frequency deviation model allows the bias voltage level to be determined based on the resonant frequency measured in act 34, the resonant frequency offset by the deviation (e.g., measured frequency*1-10 ppm), and the gap estimate.

In the example of FIG. 1, an additional safety margin is incorporated into the method to ensure that non-linear operation is avoided. The bias voltage level estimate generated in act 38 is modified by the safety margin. For example, the safety margin may be 100 mV, in which case the bias voltage level estimate is lowered by that amount. The resonant frequency of the MEMS resonator device is then measured at that lowered level in act 40.

A final value for the gap size is calculated in act 42 based on the bias levels and corresponding resonant frequencies using the frequency deviation model. As in the gap estimation described above, the frequency deviation model may be solved for a specific gap size by combining (e.g., subtracting) two instances of the frequency deviation model to cancel out the zero-bias frequency term. The subtraction may leave a polynomial expression as a function of gap size, as described further in the example below. Other techniques for resolving the gap size given the bias levels and corresponding resonant frequencies may be used.

Figure 2:
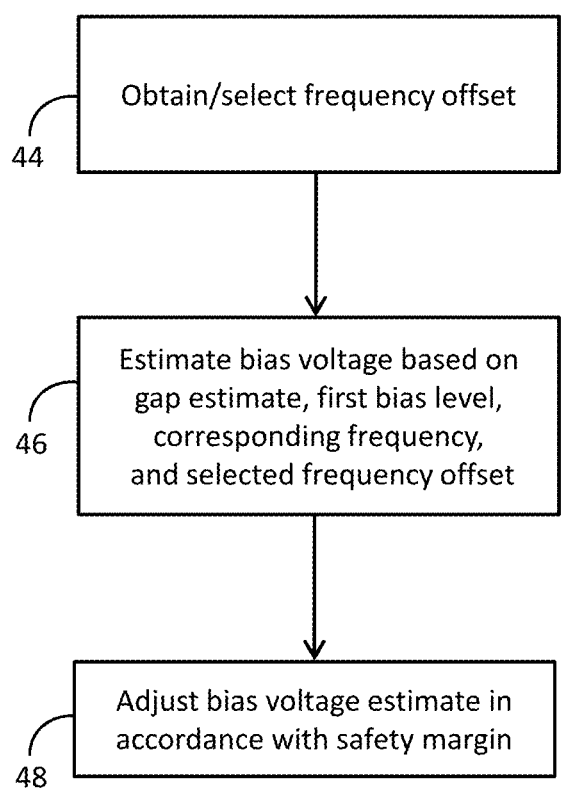
FIG. 2 is a flow diagram of an exemplary method of estimating a bias voltage for the MEMS resonator based on a frequency offset or deviation in accordance with one embodiment.

FIG. 2 depicts an embodiment in which the frequency offset may be specified. Specifying the frequency offset may allow the calibration of the MEMS resonator device to target an optimal or desired operation point. In this example, the optimal or desired operation point is specified via a certain frequency offset. The frequency offset may be specified or obtained in act 44. For example, a user may be given an option to specify the frequency offset for use with the frequency deviation model. The frequency offset need not be specified via ppm in frequency, and instead may be characterized indirectly via one or more other operational variables. For example, the non-linear behavior of the MEMS resonator may lead to one or more other effects that may be captured and/or modeled, and then used accordingly in determining a desired bias voltage level. In some cases, the data received in act 44 may then be converted to a frequency offset value to determine the corresponding deviation in frequency.

The selected frequency offset (or other data indicative of the deviation induced by the bias voltage) may then be used in act 46 to estimate the bias voltage that gives rise to the selected offset, as described above. The operational level of the bias voltage may be determined from the selected offset in other ways.

The bias voltage estimate may then be adjusted in act 48 in accordance with a safety margin, as described above.

Figure 3:
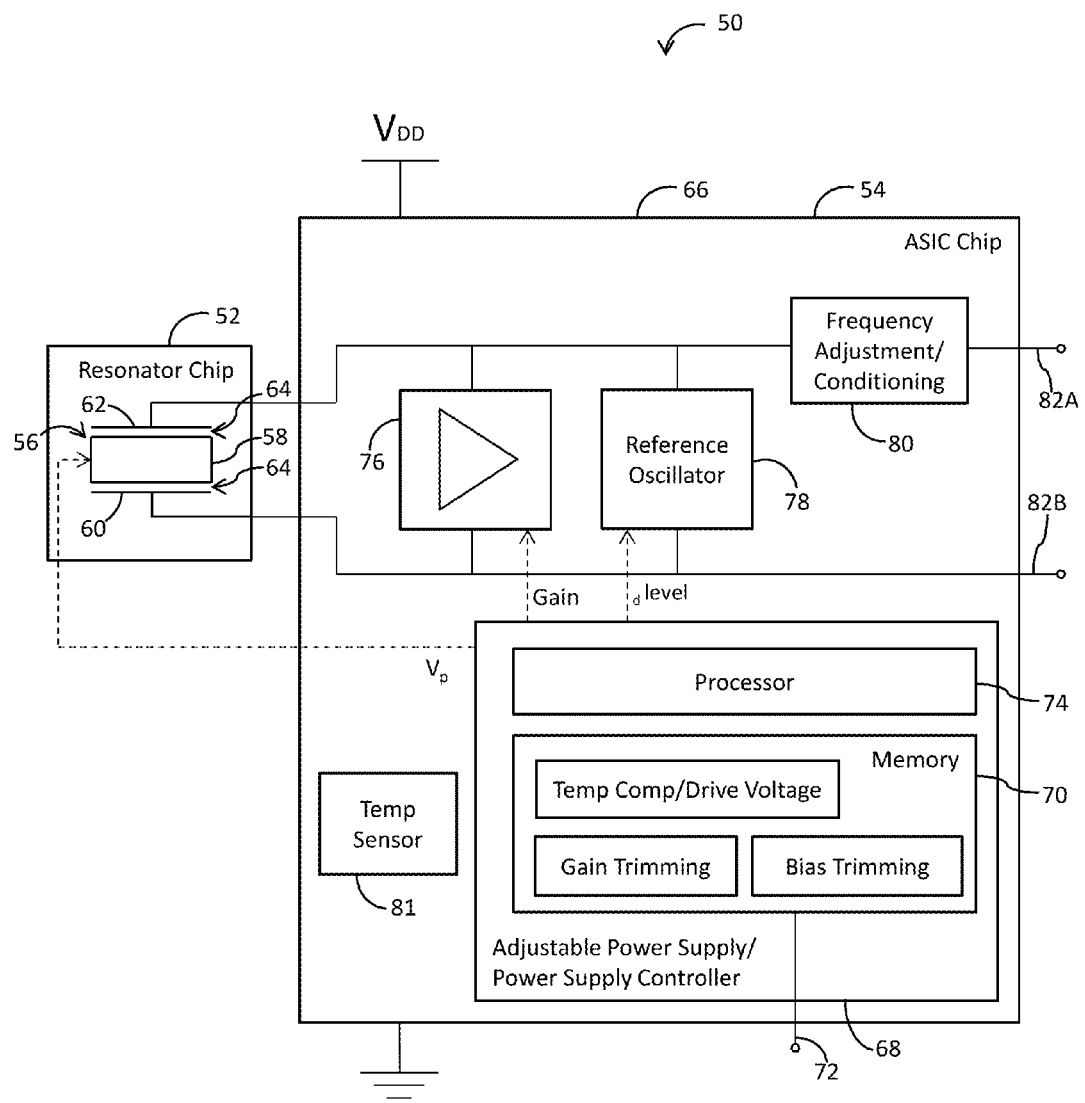
FIG. 3 is a block diagram of an exemplary MEMS resonator device configured to operate at an adjustable or configurable bias voltage level.

FIG. 3 shows an exemplary MEMS resonator device 50 constructed in accordance with one embodiment. In this example, the components of the MEMS resonator device 50 are distributed over, and disposed on, a resonator chip 52 and an integrated circuit chip 54, such as an application-specific integrated circuit (ASIC) chip. The resonator chip 52 may be encapsulated separately from the ASIC chip 54 to provide a vacuum or near vacuum operating environment for the vibrating components of the MEMS resonator device 50. The resonator chip 52 and the ASIC chip 54 may be coupled via a number of wire bonds, or any other connection. The resonator chip 52 and the ASIC chip 54 may be mounted to one another or otherwise integrated to any desired extent. Alternatively, the components of the MEMS resonator device 50 are disposed on a single chip.

The MEMS resonator device includes a MEMS resonator 56, which, in turn, includes a resonant structure 58 configured for vibration above a substrate to which the resonant structure 58 is anchored. The vibration of the resonant structure 58 is driven and/or sensed by one or more electrodes. In this example, the MEMS resonator 56 includes a drive (or input) electrode 60 and a sense (output) electrode 62, each of which is spaced from the resonant structure 58 by a gap (or gaps) 64. Additional drive and/or sense electrodes may be provided. The size of the gap(s) is determinative of the electrostatic transduction of the MEMS resonator 56. The gap(s) 64 are depicted schematically in FIG. 3, and need not be horizontally oriented or positioned as shown. For example, the resonant structure 58 may be disposed above the electrodes 60, 62, in which case the gap(s) 64 is vertically oriented. In resonator designs having more than one gap, the sizes of the gaps may vary somewhat between electrodes. In these cases, and when or a gap varies over its length, the gap size of the resonator model may be an effective gap size for the MEMS resonator 56.

The MEMS resonator device 50 includes a control circuit 66 coupled to the MEMS resonator 56. In this example, the control circuit 66 is disposed on the ASIC chip 54, but may integrated with the MEMS resonator 56 and/or the MEMS resonator chip 52 to any desired extent. The control circuit 66 is configured to control and supply a bias voltage, $V_p$, applied to the resonant structure 58, as well as an excitation voltage, $v_d$, applied to the drive electrode 60. The bias voltage, $V_p$, and the excitation voltage, $v_d$, are developed and/or supplied by an adjustable power supply or power supply controller 68 of the control circuit 66. In this example, the bias voltage, $V_p$, is generated and supplied by the adjustable power supply 68. The adjustable power supply 68 may also be configured to determine the level of the bias voltage.

In the embodiment of FIG. 3, the adjustable power supply 68 of the control circuit 66 includes a memory 70 in which various configuration or calibration data is stored. For example, the configuration data includes bias trimming data indicative of the bias voltage level, gain trimming data, and temperature compensation data. Additional, fewer, or alternative trimming or configuration data may be stored in the memory 70, or in some other device or component of the control circuit 66. The temperature compensation data may include data directed to determining the excitation signal amplitude as a function of operating temperature. Other data indicative of the excitation amplitude may also or alternatively be stored in the memory 70.

The memory 70 is configurable to adjust the configuration data, including the data indicative of the bias voltage level. For example, new data indicative of the bias voltage level may be written to the memory 70 for storage therein. Any old data indicative of the bias voltage level may be overwritten or otherwise erased. The adjustable power supply 68 includes one or more configuration ports 72 coupled to the memory 70 to store and update the data indicative of the bias voltage. In one embodiment, the configuration port(s) 72 is a serial data port. The data in the memory 70 may be modified to adjust the bias voltage level, the excitation amplitude, and other operational point parameters via the configuration port(s) 72 in a variety of ways. In one example, the memory 70 includes an electrically erasable programmable read-only memory (EEPROM) coupled to the configuration port(s) 72. The data indicative of the bias voltage level may be modified by applying one or more program signals to the memory 70 via the configuration port(s) 72. In one example, the memory 70 includes a number of one-time programmable or otherwise non-volatile memories integrated within the ASIC chip 54.

The memory 70 may include any number or type of memories or memory devices. The configuration data may be distributed in any arrangement across the memories or memory devices.

The adjustable power supply 68 of the control circuit 66 includes a processor 74 coupled to the memory 70 and configured to access the data indicative of the bias voltage. The processor 74 may be further configured to develop the bias voltage in accordance with the data. The processor 74 may control one or more voltage regulator or other circuits (not shown) of the adjustable power supply 68 to develop the bias voltage. Alternatively, the processor 74 may have integrated voltage regulation or other functionality to generate the bias voltage directly. In one example, the processor 74 includes a number of control logic state machines in one or more components of the ASIC chip 54. The processor 74 may include any number or type of processors.

The processor 74 may use the data stored in the memory 70 to set the bias voltage at an optimal or desired level as described above. The data may be stored in the memory 70 as a result of the implementation of one of the configuration methods described above. The data may thus be reflect parameters or characteristics of the MEMS resonator device 56, including, for instance, the thickness of the resonant structure 58 and an estimate of the gap 64. The data may thus also reflect the frequency deviation model of the MEMS resonator 56, as well as an operational point for the MEMS resonator 56, such as the operational point at which the frequency deviation model indicates a frequency offset of about 10 ppm.

The processor 74 may be programmed via one or more instruction sets stored in the memory 70. The processor 74 and the memory 70 form a power supply controller of the MEMS resonator device 50 through implementation of the instruction set(s) by the processor 74. For example, implementation of the instruction set(s) may include or involve controlling an amplifier 76 of the control circuit 66. The amplifier 76 is coupled to the MEMS resonator 56 to amplify an output signal of the MEMS resonator 56. The amplification may be controlled in accordance with a gain level signal generated by the processor 74 or other component of the adjustable power supply 68 controlled thereby. The gain is applied across the output terminals of the MEMS resonator 56 to sustain vibration of the MEMS resonator 56. In some cases, the gain level output of the adjustable power supply 68 provides power to the amplifier 76 to support the amplification. Alternatively or additionally, the amplifier 76 receives power directly from a power source $V_{DD}$ for the control circuit 66.

The processor 74 may be programmed via one or more instructions sets stored in the memory 70 to act as a power supply controller in connection with a reference oscillator 78 of the control circuit 66. The excitation voltage, $v_d$, is generated by the reference oscillator 78. The reference oscillator 78 is configured to generate the excitation voltage at an amplitude determined by an output of the adjustable power supply 68. For example, the adjustable power supply 68 provides an excitation level signal to the reference oscillator 78 to establish the drive level for the MEMS resonator 56 via the amplitude of the excitation voltage, $v_d$.

The processor 74 may be programmed via one or more instructions sets stored in the memory 70 to control one or more other components of the control circuit 66. For example, the control circuit 66 may include one or more circuit components 80 directed to frequency adjustment and/or conditioning. The circuit components 80 may receive the output of the MEMS resonator 56 to adjust the frequency. For example, the adjustments may include a frequency multiplier, frequency synthesizer, phase locked loop, or other circuit driven by the output of the MEMS resonator 56. One or more of such circuits may be directed to adjusting the output frequency of the MEMS resonator device 50 in accordance with one or more temperature compensation techniques. The control circuit 66 may include a temperature sensor 81 to provide an indication of the operating temperature of the MEMS resonator 56 to the processor 74 or other component of the control circuit 66. Further details regarding exemplary temperature compensation techniques and frequency adjustment circuitry are set forth in U.S. Pat. No. 7,449,968 ("Frequency and temperature compensation synthesis for a MEMS resonator"), the entire disclosure of which is incorporated by reference.

The circuit components 80 develop an oscillator signal over a pair of oscillator output terminals 82A, 82B of the control circuit 66. The oscillator output terminals 82A, 82B may be driven directly or indirectly by the MEMS resonator 56. The circuit component 80 may be a phase locked loop that converts resonator frequency (e.g., 18 MHz) to any target frequency (e.g., 125 MHz). The circuit component 80 may have temperature compensation function in order to adjust resonator frequency variation across temperature.

The construction, configuration, and other characteristics of the memory 70 of the adjustable power supply 68 may vary from the example described above. The memory 70 need not store the data indicative of the bias voltage level digitally or via solid-state circuitry. For instance, the memory 70 may include a potentiometer, a set of switches (e.g., dual-in-line (DIP) switches), a set of pins coupled to respective circuits (e.g., resistive paths), and/or other components to specify the bias voltage level.

The resonant mode, design, configuration, and construction of the MEMS resonator 56 may vary. The resonant structure 58 may have any shape, and may be disposed in a cantilevered, suspended, or other spaced relationship relative to the drive electrode 60 and the sense electrode 62. The drive and sense electrodes 60, 62 are disposed adjacent the resonant structure 58 such that the MEMS resonator 56 is electrostatically transduced, in which the resonant structure 58 resonantly vibrates in the gap 64. The resonant structure 58 may include one or more conductive materials, surfaces, and/or regions for electrostatic excitation via the AC input or drive signal $v_d$ applied to the drive electrode 60. The resonant structure 28 may be enabled or activated for such vibration by applying the DC bias voltage V, between the resonant structure 58 and one or both of the electrodes 60, 62 and/or the substrate to which the MEMS resonator 56 is anchored. The bias voltage $V_p$ may be used to pull down or otherwise draw the resonant structure 58 toward the electrodes 60, 62 to promote vibration, increase stiffness, resonant frequency, etc. The excitation of the resonant structure 28 results in vibration at a fundamental (or other) resonant frequency of the resonant structure 28. The output of the MEMS resonator 56 is sensed by the sense electrode 62 in this example as a sense current $i_o$.

The resonant structure 58 may be anchored to the substrate via a number of support arms (not shown), which may be attached to the resonant structure 58 at nodal points of the fundamental or other desired resonant mode achieved during operation. Thus, in some cases, the MEMS resonator 56 is configured with free rather than fixed ends, a so-called free-free resonator arrangement that minimizes losses to the substrate, but other embodiments may include one or more clamped or otherwise fixed ends.

In some examples, the resonant structure 58 is beam-shaped for a flexural mode of vibration. The vibration mode primarily includes movement in a direction vertical or transverse to the plane of the substrate. The electrodes 60, 62 and the resonant structure 58 may be oriented relative to one another for vibration of the resonant structure 58 transverse to the substrate. In other examples, the flexural mode of vibration includes movement in a direction lateral or parallel to the plane of the substrate. The vibration mode need not be flexural and instead may be based on movement involving, for instance, expansion and contraction of the resonant structure 58. The resonator frequency models described and referenced herein may be adjusted accordingly.

The above-described components of the MEMS resonator 58 may be formed via surface micromachining fabrication techniques. The electrodes 60, 62 and the resonant structure 58 may be made of polysilicon or other conductive materials. The polysilicon regions of the structures may be doped (e.g., n-type or p-type) to a dopant concentration sufficient to reach a desired conductivity level.

Further details regarding examples of the MEMS resonator 56, one or more of its constituent structures, and/or the fabrication of the MEMS resonator 56 and/or its constituent structures may be found in U.S. Pat. Nos. 6,249,073 ("Device including a micromechanical resonator having an operating frequency and method of extending same") and 6,930,569 ("Micromechanical resonator having short support arms"), the entire disclosures of which are incorporated by reference. The MEMS resonator 56 is shown in schematic form for convenience in illustration, and may include a number of other components in certain applications or operational configurations.

The temperature compensation features of the device 20 may be combined with one or more other temperature compensation techniques (e.g., mechanical, electrical, oven-based, etc.), such as those described in U.S. Patent Publication No. 2002/0069701 ("Micromechanical resonator device") and U.S. Pat. No. 7,449,968 ("Frequency and temperature compensation synthesis for a MEMS resonator"), the entire disclosures of which are incorporated by reference.

Figure 4:
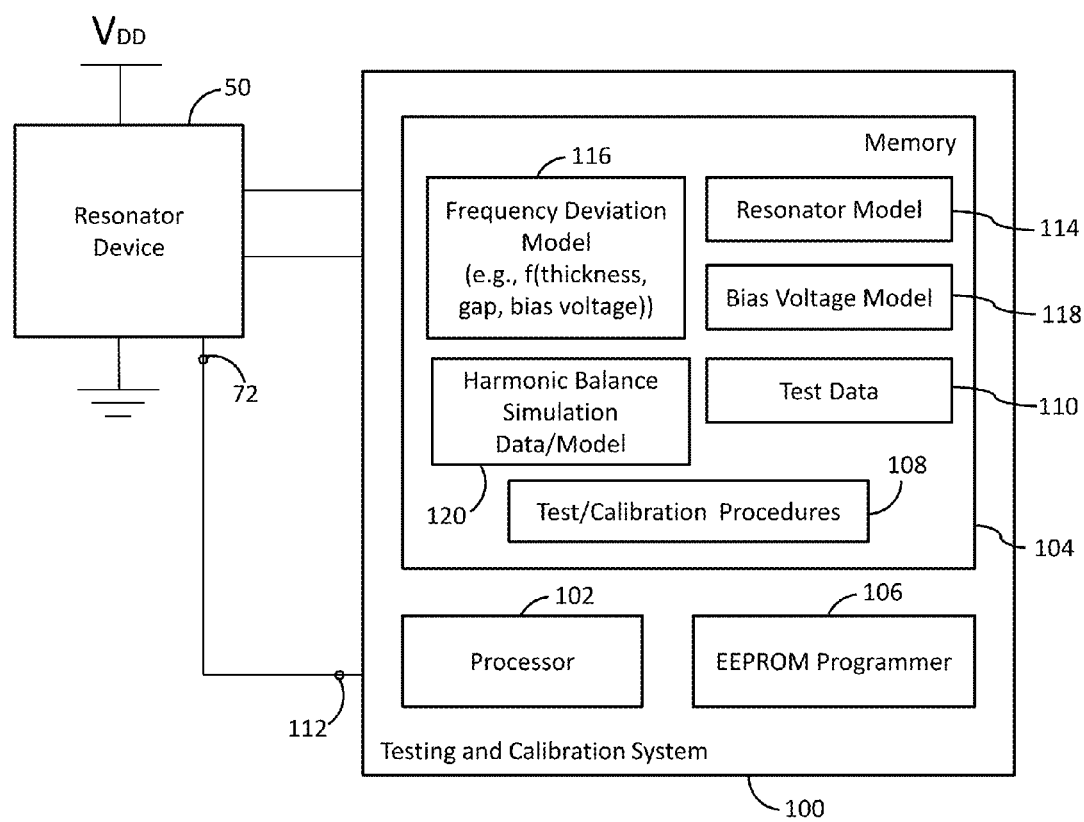
FIG. 4 is a block diagram of a system configured to test, calibrate, and/or configure a MEMS resonator device in accordance with one embodiment.

FIG. 4 depicts a testing and calibration system 100 for configuring the MEMS resonator device 50. The testing and calibration system 100 may be operable to implement the above-described calibration methods. The MEMS resonator device 50 may be configured by the testing and calibration system 100 by determining and storing the bias trimming and other data that establishes an optimal or desired operational point as described above. In this example, the testing and calibration system 100 includes a processor 102, a memory 104, and an EEPROM writer 106. Additional, fewer, or alternative components may be included.

The processor 102 is operable to implement one or more test and/or calibration procedures on the MEMS resonator device 50. Data indicative of one or more instruction sets 108 directed to the test and/or calibration procedures may be stored in the memory 104 for execution by the processor 102. Implementation of the test procedures by the processor 102 generates test data 110, which may be stored in the memory 104. The test data may be processed by the processor 102 in connection with implementing the calibration procedures. The processor 102 may configure the MEMS resonator device 50 by generating one or more calibration output signals via one or more output terminals 112 coupled to the configuration port(s) 72 of the MEMS resonator device 50.

Data representative of the above-described MEMS resonator models may be stored in the memory 104. The model data may be stored in tables (e.g., look-up tables), databases, other arrangements that relate the above-referenced parameters. The models may be based on theory, simulation data; empirical data, or any combination thereof. The model data may be stored as one or more datasets including, for instance, resonant frequency data at various operational points. The model data may alternatively or additionally be indicative of one or more formulas or characteristics. The formula (s) may be used by the processor 102 to calculate one or more of the device or operational parameters referenced above, including the bias voltage level. In this example, the memory 104 includes data representative of a resonator frequency model 114, a frequency deviation model 116, a bias voltage model 118, and harmonic balance simulation data 120. Further details regarding such model data are described below in connection with an example embodiment.

In some examples, including the beam-shaped flexural mode resonators referenced above, the resonator frequency model can be described as $$f = f_0 \left(1 - \frac{k_e}{k_m}\right)^{1/2} = f_0 \left(1 - \frac{V_P^2 \varepsilon_0 A_e}{d_0^3 k_m}\right)^{1/2} \text{ where } f_0 = 1.03 \sqrt{\frac{E}{\rho}} \frac{h}{L^2} \quad (1)$$

where $f_0$ is the resonator frequency without bias, E is the Young's modulus, $\rho$ is the density of resonator material, h and L are the thickness and length of the resonator, respectively. Parameters in the equation such as the area of the electrode ($A_{electrode}$), dielectric constant in vacuum ($\varepsilon_0$), spring constant of the resonator ($k_m$), and the mass of the resonator (m), are less sensitive to temperature variation. As described herein, the bias voltage of the resonator ($V_P$) is a variable that may be controlled by the disclosed circuitry to, in turn, control or establish the resonator operation point. Such use of the bias voltage is not limited to this exemplary resonator frequency model.

Figure 5:
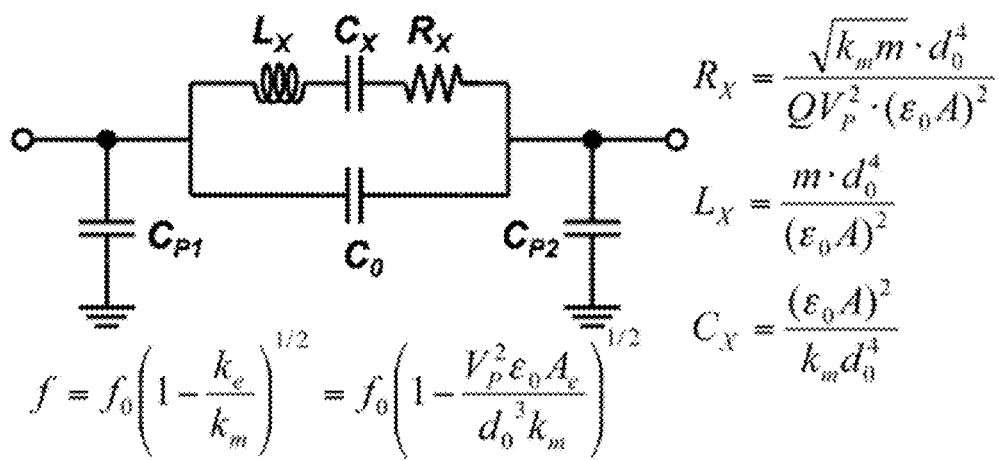
FIG. 5 is a schematic diagram of a MEMS resonator model.

FIG. 5 depicts a small signal equivalent circuit of a MEMS resonator that addresses the parameters that lead to the exemplary frequency model. Two parameters of the MEMS resonator equivalent circuit are sensitive. The air gap between driving electrode and resonator ($d_0$) is sensitive to the manufacturing process. The quality factor (Q) is sensitive to temperature. Therefore, the motional impedance ($R_x$) of the MEMS resonator is sensitive to both temperature and manufacturing process variation because it is proportional to the fourth order of $d_0$ and inversely proportional to Q. The oscillator circuits described herein often have a transimpedance gain larger than $R_x$ in order to initiate and sustain the oscillation.

Within an acceptable semiconductor manufacturing tolerance of thin film deposition, the motional impedance of such MEMS resonators may vary by a factor of 7.5, and Q may vary a factor of 4 across temperature from –55° C. to 125° C. In order to compensate for such variation across all environmental conditions, the disclosed MEMS resonators are tuned or calibrated to operate at the right operation point in order to avoid performance degradation and failed oscillation.

Once oscillation of the MEMS resonator is sustained, the key aspect of the resonator vibration is the vibration amplitude (mechanical displacement during vibration) of the resonator. The vibration amplitude |x| is expressed by $$|x| = \frac{Q}{k_m} V_P |v_i| \frac{\varepsilon_0 A}{d_0^2} \quad (2)$$

where $|v_i|$ is the ac driving voltage on the driving electrode (referred to as $v_d$ above). As shown, |x| is dependent on $d_0$ as well as Q. Therefore |x| is sensitive to both process variation and temperature variation.

For MEMS resonators with electrostatic transduction, |x| is tuned to an optimal or desired point via the disclosed configuration methods. Increasing $V_P$ and $v_i$ results in better oscillator phase noise for oscillators. However, increasing $V_P$ and $v_i$ makes large |x|. If |x| is greater than, for instance, 10% of $d_0$ as shown in FIG. 6, the force F applied to the resonator may no longer be linear (or sufficiently linear).

$$\text{Linear:} \quad F_{ab} = -\frac{\varepsilon_0 A V_P V_1}{d_0^2} \text{ while vibration amplitude is small} \quad (3)$$
$$\xrightarrow{|x| \ll d_0}$$

$$\text{Non-Linear} \quad F = \frac{(V_P + v_1)^2}{2} \cdot \frac{\partial C}{\partial x} = -\frac{\varepsilon_0 A (V_P + v_i)^2}{2} \cdot \frac{\partial (d_0 + x)^{-1}}{\partial x}$$

Figure 6:
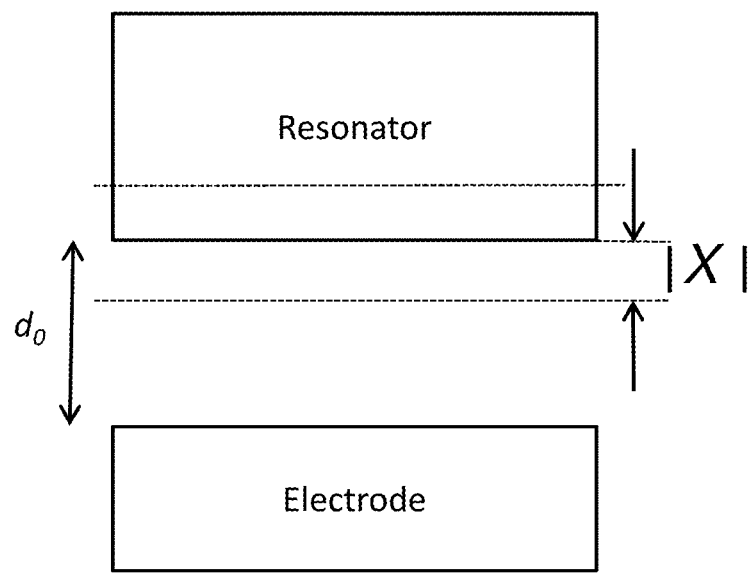
FIG. 6 is a schematic diagram of a MEMS resonator device to define a vibration amplitude of the device.

While the force is not linear, the resonator spectrum bends over the left as shown in the amplitude vs. frequency plot of FIG. 6. The peak frequency of the resonator spectrum then decreases with the power (thus the vibration amplitude) applied to the driving electrode as shown in the frequency deviation vs. input power plot of FIG. 6.

If the MEMS resonator is operated with large |x|, spurious vibration may be excited due to nonlinear forces applied to the resonator. Not only may the overall phase noise be degraded, but there may also be frequency stability issues from bifurcation, and potentially lifetime issues with overflexing.

Therefore, in order to have desirable phase noise performance, the maximum |x| may be determined so that the resonator is not in nonlinear mode. This amplitude may be kept constant across temperature in order to maintain a constant oscillator phase noise at all temperatures. For example, the vibration amplitude of a resonator may vary by a factor of 6 in the temperature range from –55° C. to 125° C. if the drive amplitude is held constant.

As shown in the frequency deviation plot of FIG. 6, it may be desirable to configure the MEMS resonator for operation at the maximum |x| by selecting the power applied to the resonator that causes a certain ppm level of frequency shift. For example, if 10 ppm is selected as the threshold, the resonator is operated with –17 dBm (across a 50 Ohm impedance) of $|v_i|$ at a fixed $V_P$ in order to have the lowest phase noise performance. If a lower ppm is selected as the threshold, e.g. 5 ppm, it may be difficult to detect the frequency shift with test equipment. Thus it may be hard to determine the power threshold. If a higher ppm is selected, e.g. 20 ppm, the resonator frequency may be sensitive to the variation of ac power applied to the resonator. Thus the resonator frequency may not be stable. Thus, in many cases, one optimal threshold is about 10 ppm.

As described above, the disclosed methods correct or address these factors by extracting device parameters, such as the resonant structure (e.g., beam) thickness and gap during a bias voltage calibration or tuning procedure. The manner in which such parameters are extracted may vary from the examples described above. The gain, phase, and ac amplitude levels driving the resonator may also be tuned or trimmed to achieve a stable oscillator across the process variations. For example, the phase may be trimmed by the control circuit by alternating the phase response of the amplifier. However, rather than maintain a constant bias voltage, the extracted parameters are used to trim the bias voltage as an alternative or additional way of attaining an optimal or desired operation point.

Figure 7:
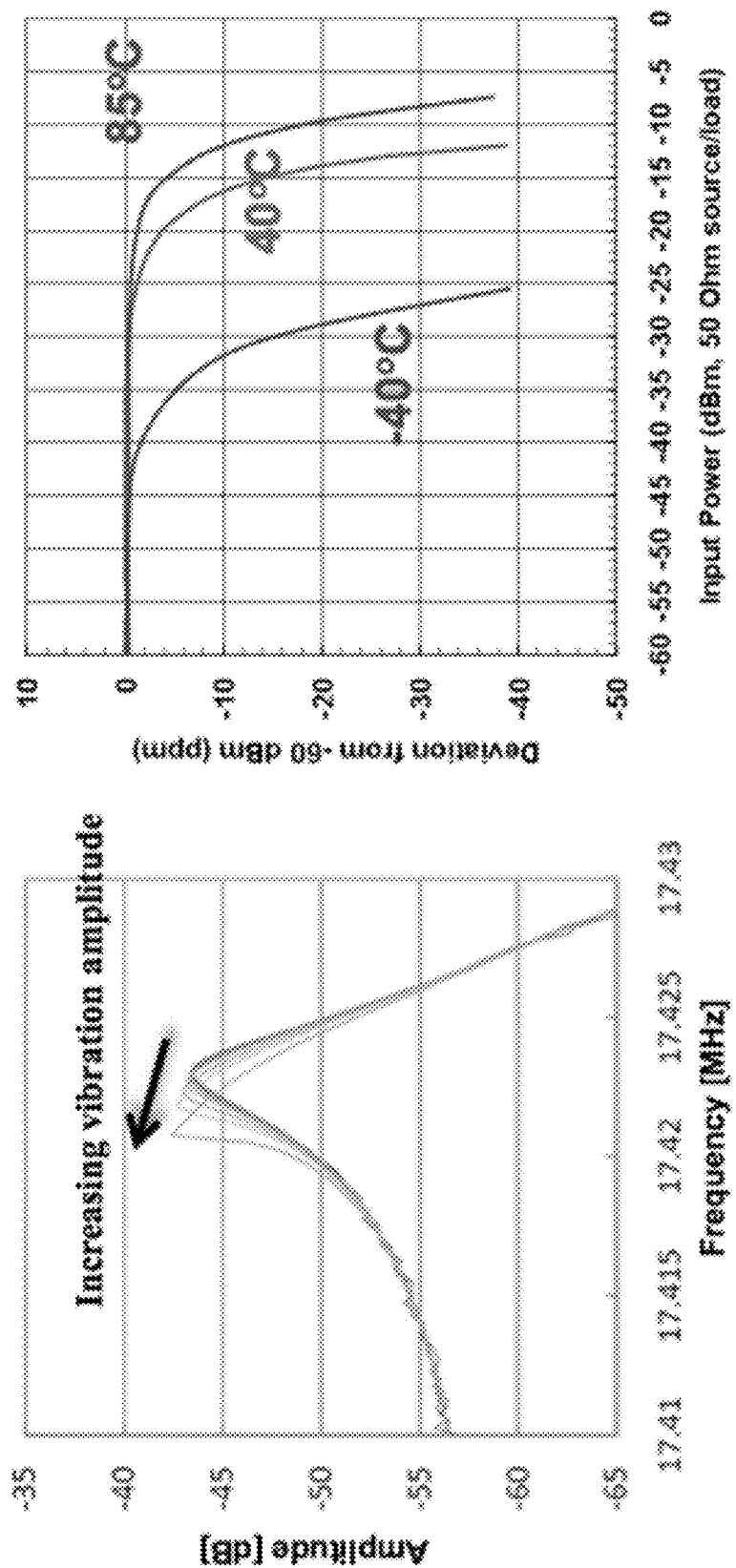
FIG. 7 shows graphical plots depicting a resonator spectrum shift and a peak frequency decrease, respectively.
Figure 8:
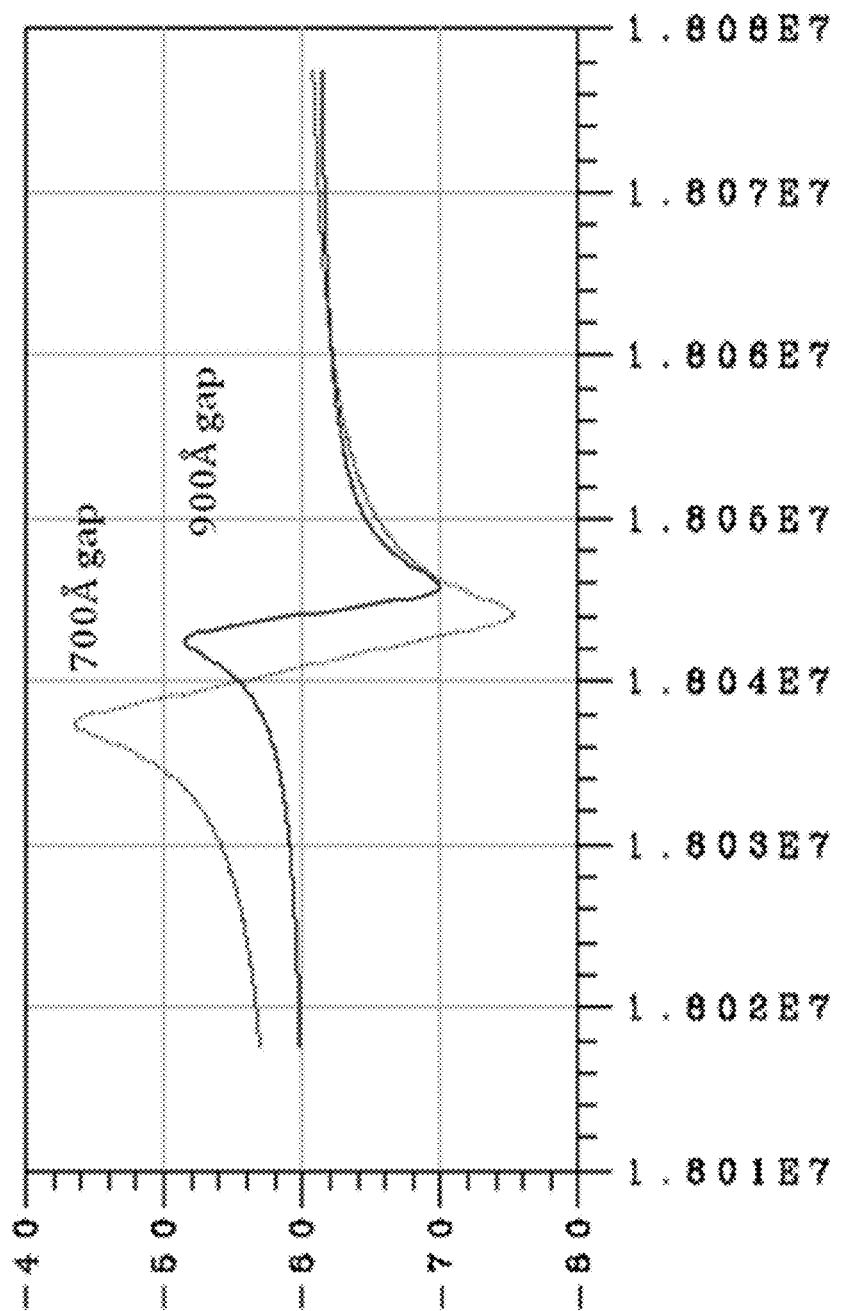
FIG. 8 is a graphical plot of a frequency sweep of a device with gap process variation.

For example, the current device gap ($d_0$) may range from 700 to 900 Angstrom. For a nominal polysilicon thickness and nominal Q of 7000, the device $R_x$ at 2.5 V of $V_P$ may range from 16 kOhms to over 45 kOhms as shown in the plot in FIG. 7, which depicts the frequency sweep of a MEMS resonator device with varying gap process variation from 700 to 900 Angstrom and a nominal polysilicon resonant structure thickness and Q factor. Such variation may benefit from a gain calibration for the oscillator circuits that sustain the oscillation, as well as a phase calibration because the weak resonance for the thick gap devices has a shallow phase dip as shown in FIG. 8, which depicts the phase transition of a MEMS resonator device biased at 2.5 V for 700, 800, and 900 Angstrom gaps. A phase calibration may address the variable depth of the phase transition.

In addition to having to calibrate the gain and phase of the device, the oscillator device may be configured via an amplitude calibration. The amplitude calibration is directed to driving the device as hard as possible without going into a large signal behavior in which the nonlinear effect leads to poor noise performance. A higher drive level may be useful for the following reasons. Thick gap devices have a high motional resistance. Therefore, to maximize power delivered from the resonator, and hence, phase noise, a high drive signal is useful. Interfering signals from the oscillator chip including, but not limited to, incoherent signals from digital logic, output buffers, internal clocks, charge pumps, etc., can corrupt the reference oscillator. To mitigate these interferers, a maximum drive level may be useful. This effect may be exacerbated by thick gap devices with high motional resistance with a large signal drop across the resonator as well as thin gap devices with very poor linearity forcing the drive levels to be extremely small.

Figure 9:
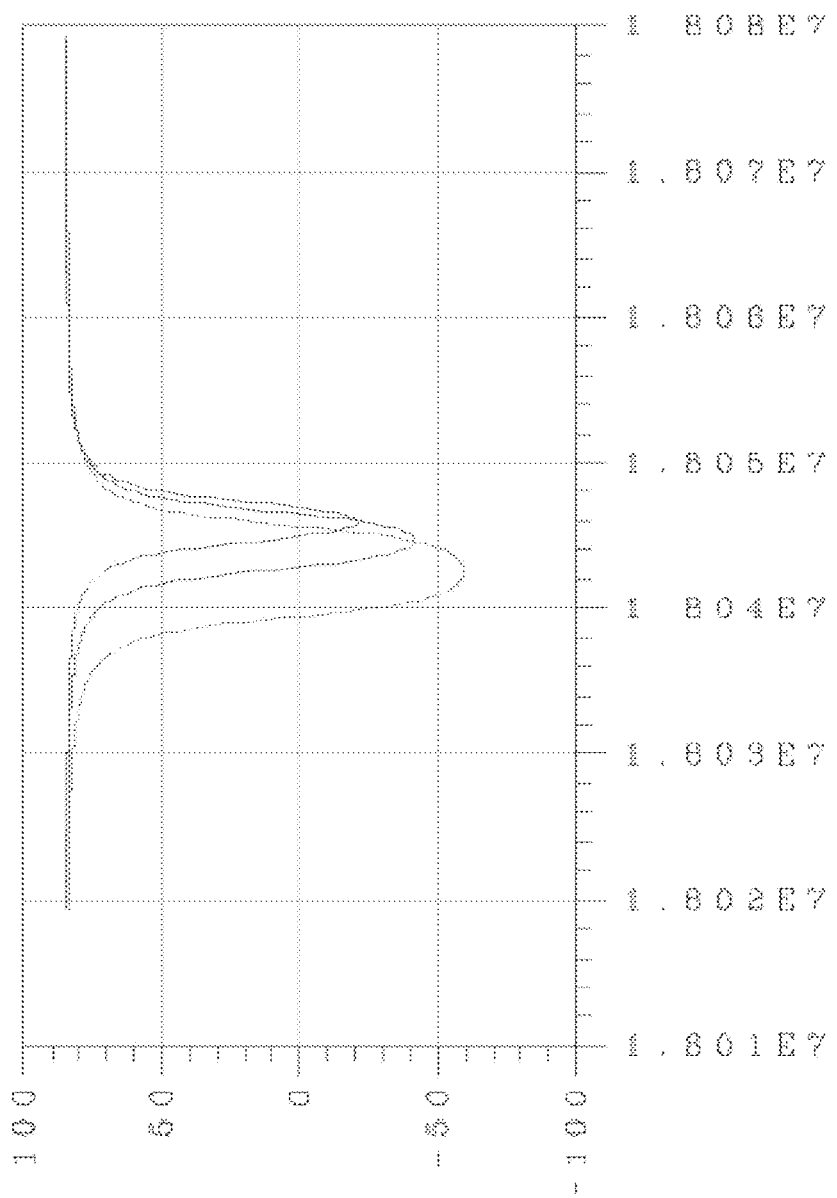
FIG. 9 is a graphical plot depicting phase transitions of a device with gap process variation.

In one example, the largest tolerable signal prior to nonlinear behavior is defined as the signal level that generates a 10 ppm shift in the resonant frequency compared to a very low drive level. This onset of nonlinear behavior is process dependent. Typical curves at −40° C. vs. process are shown in the chart of FIG. 9, which depicts drive level dependent curves for operation with a resonant structure thickness of 2 micron and nominal Q. As shown in this chart, the setting of the drive level is process dependent and has a wide range for the control circuitry (e.g., the oscillator ASIC chip) to support.

Figure 10:
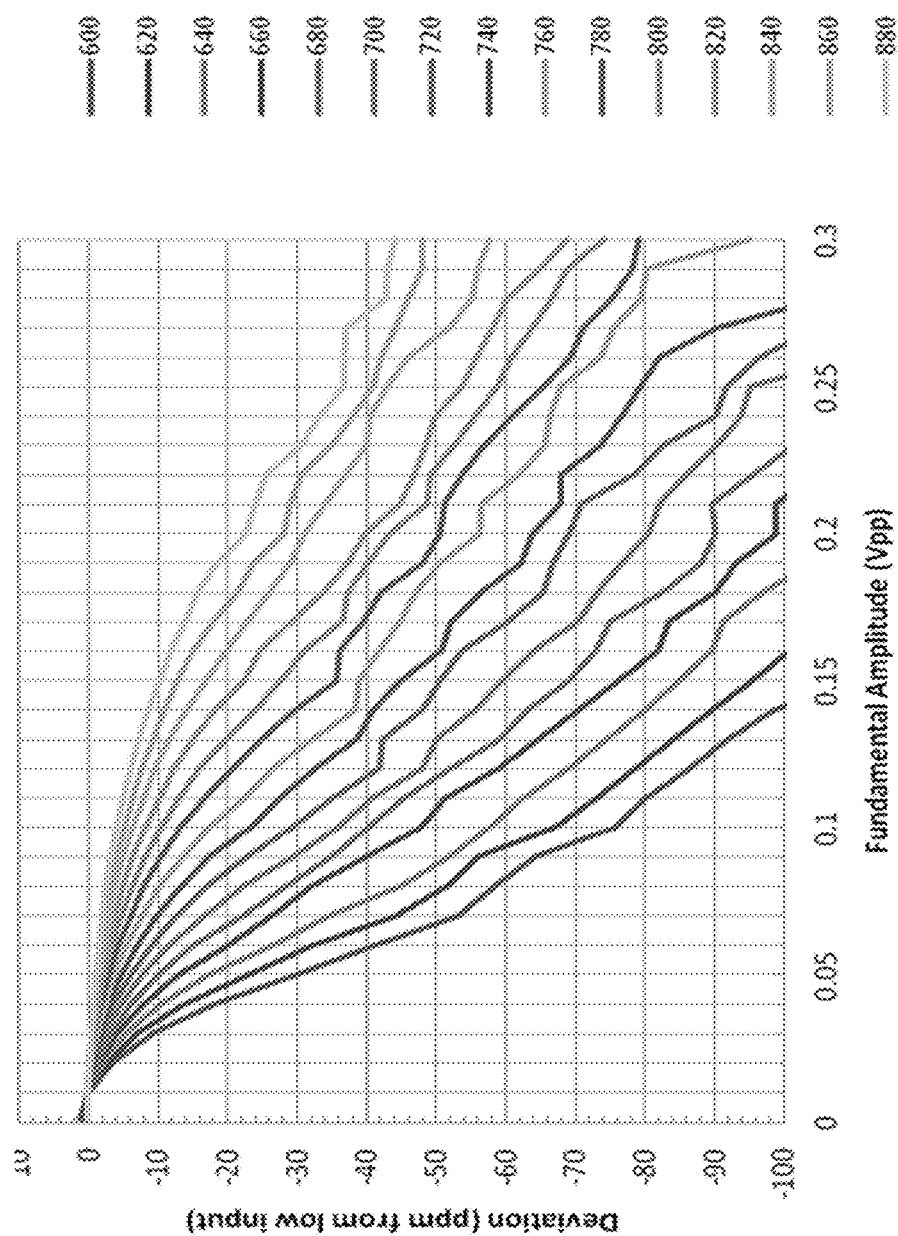
FIG. 10 is a graphical plot depicting drive level dependent curves for a number of gap sizes.

In addition to having a wide range at −40° C. where the drive level is set (e.g., the most sensitive temperature), the optimal drive level is also a strong function of temperature. FIG. 10 shows the optimal drive level vs. temperature for exemplary gap sizes. This varies across fabrication process. In addition, the slope of the drive level vs. temperature is also a function of fabrication process. This leaves the choice of either having a slope that is process dependent or simply not driving the resonator at the optimal level for thicker gap devices making it more sensitive to power supply noise, interference, and degraded phase noise.

Rather than attempting to address all of these deficiencies of process dependent effects through drive, gain, and amplitude trimming, the disclosed devices and methods address these deficiencies through trimming the bias voltage ($V_P$) of the device (either as an alternative or in addition to such trimming). One exemplary, model-based approach to support the bias voltage trimming is described below.

Figure 11:
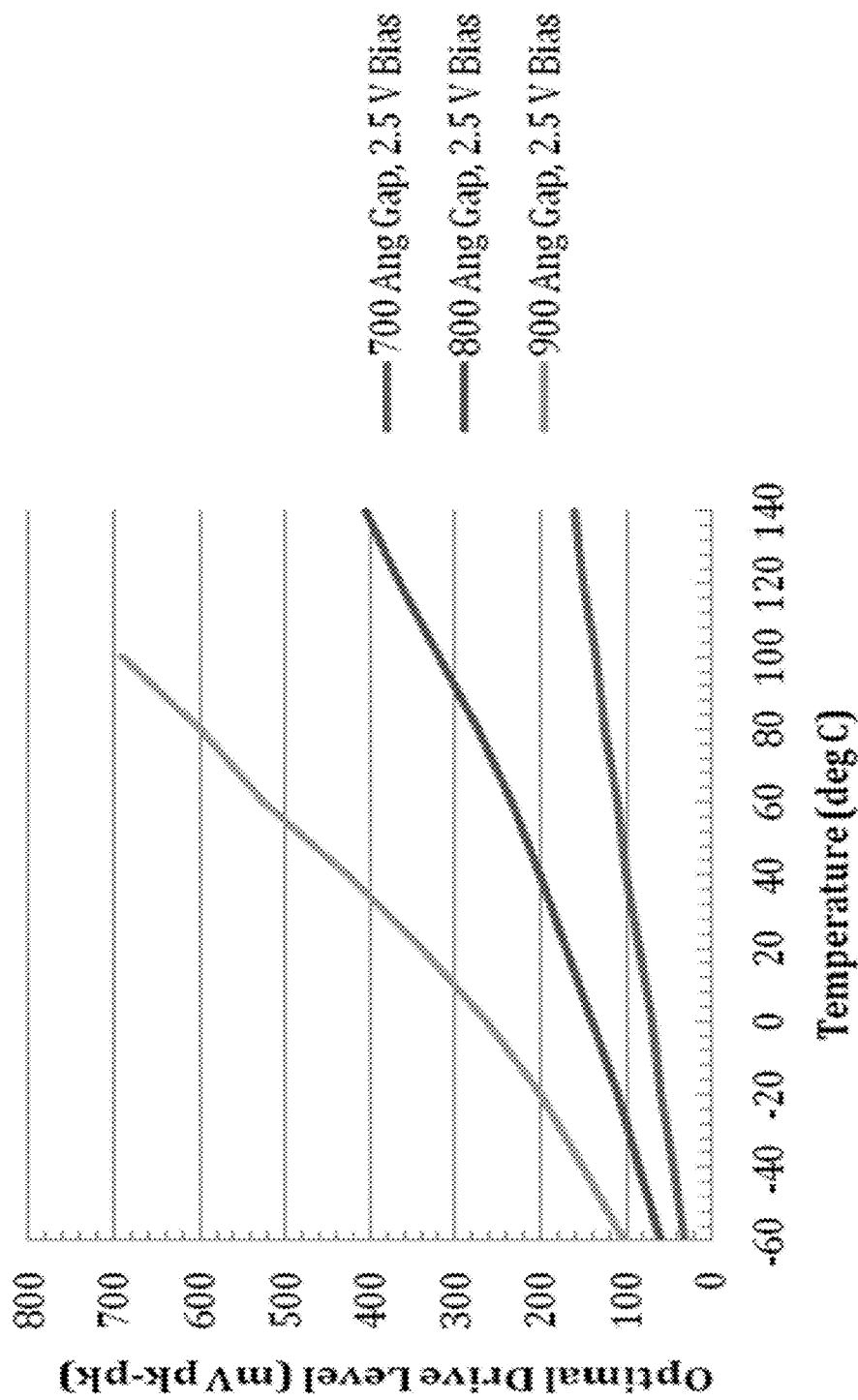
FIG. 11 is a graphical plot depicting optimal drive levels for various gaps.

FIG. 11 depicts the data underlying one example of a frequency deviation model of a MEMS resonator (i.e., deviation from the zero-bias frequency induced by the bias voltage), which may be built based on any combination of theory, simulation, and testing data. In this example, frequency deviation is a function of resonator thickness, gap, and bias voltage. The model may be expressed via an exemplary equation as follows:

$$\text{Deviation[thickness\_,gap\_,bias\_]}:=-585.9788404205713+91.94512551106672\,\text{bias}-49.01004996575902\,\text{bias}^2+7.646989795857664\,\text{bias}^3+3.5365693852289023*10^{12}/\text{gap}^{3.5}-(2.1908765561429941*10^{12}\,\text{bias})/\text{gap}^{3.5}+(2.026933891249052*10^{11}\,\text{bias}^2)/\text{gap}^{3.5}-(2.817595340000418*10^{11}\,\text{bias}^3)/\text{gap}^{3.5}+524.9949375333746\,\text{thickness}-128.35887641004095\,\text{thickness}^2-0.14845550350682987\,\text{bias}^3\,\text{thickness}^2-(4.191262351418572*10^{11}\,\text{thickness}^2)/\text{gap}^{3.5}+(3.178792115139883*10^{11}\,\text{bias}\,\text{thickness}^2)/\text{gap}^{3.5}-(7.747520818845824*10^{10}\,\text{bias}^2\,\text{thickness}^2)/\text{gap}^{3.5}+(3.768913729544499*10^{10}\,\text{bias}^3\,\text{thickness}^2)/\text{gap}^{3.5} \quad \text{(Equation 4)}$$

An optimum bias point vs. process relationship may be constructed using the nonlinear model for the resonator with a harmonic balance simulation as follows:

a. Set a given process combination.

b. Estimate a bias level.

c. Analyze the output frequency while sweeping drive level and compare the 200 mV peak-peak frequency deviation to the 1 mV peak-peak frequency deviation (which is safely within the linear region of operation). A 200 mV drive level is one example of a convenient drive level. Other drive levels may be used.

d. If the frequency deviation at 200 mV peak-peak is too low, increase bias and repeat step 3. If the frequency deviation at 200 mV peak-peak is too high, decrease bias. Continue this iteration until the deviation is 10 ppm +/−1 ppm. The final bias level may be referred to as the optimal bias level.

Figure 12:
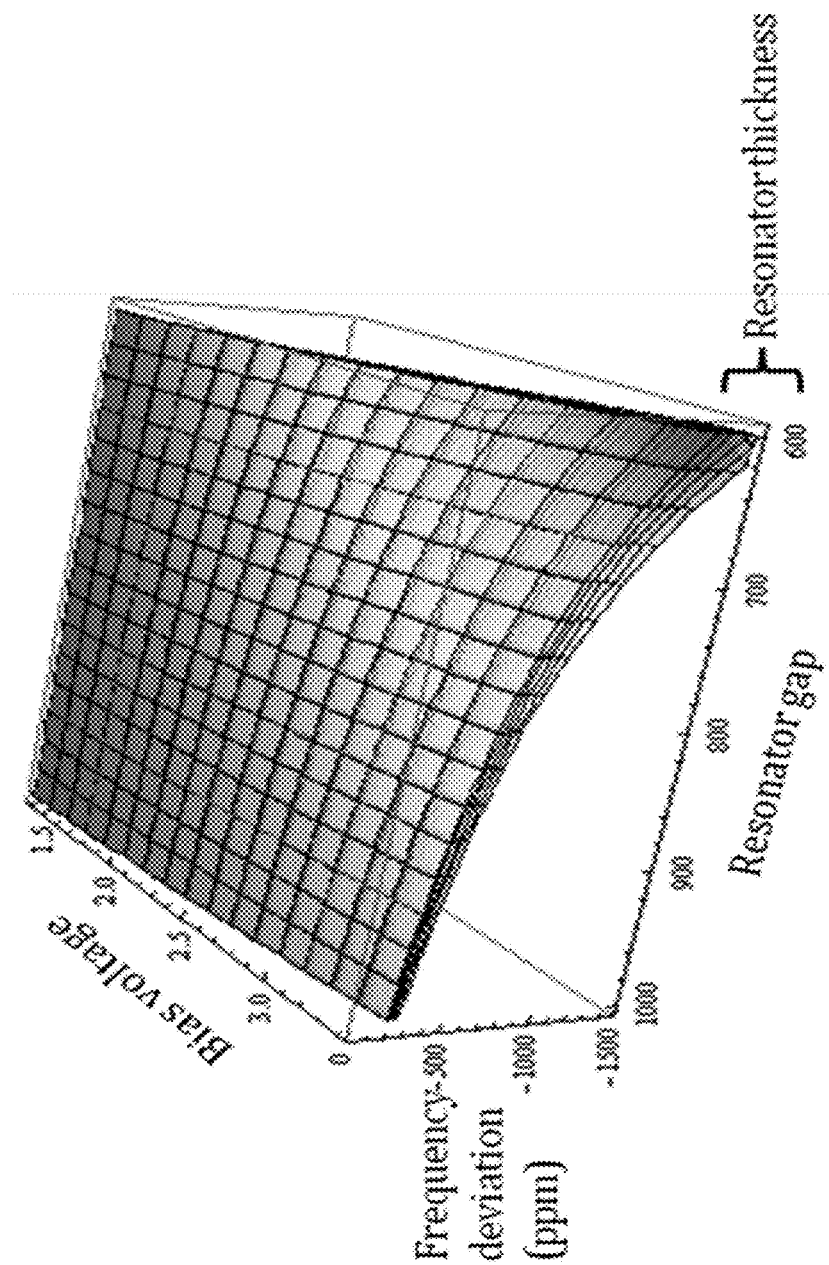
FIG. 12 is a graphical plot depicting frequency deviation as a function of bias voltage, resonator gap, and resonator thickness.

FIG. 12 depicts a plot of the resulting optimal bias voltage levels for various device parameter combinations. In this example, the parameter combination is gap size and resonator thickness. The plot and the underlying data provide a model for the optimal bias voltage level given a particular device parameter set. Once the data values are determined, the bias voltage level calculation may be mapped to an equation for use by the test and calibration system described above. In one example, the equation is as follows:

$$\text{OptBias(thickness,gap)}=0.047758+0.119405\times\text{thickness}-0.11904762\times\text{thickness}^2-0.00349997\times\text{gap}+0.001414\times\text{Thickness}\times\text{gap}+4.09955\times10^{(-6)}\times\text{gap}^2 \quad \text{(Equation 5)}$$

where the thickness is in microns and the gap is in Angstrom. In one example, the above equation maps the bias calculation to better than 50 mV across all process variations.

Any one or more of the above models may be tabulated or otherwise captured for storage in the memory of the test and calibration system for use in conjunction with the calibration process, an example of which is set forth below.

During calibration, resonator device parameters are extracted as follows:

a. At room temperature, turn on the circuit, and apply a bias voltage on the resonator till the oscillator oscillates. This bias voltage is referenced as resbiasmin.

b. Increase the bias by 100 mV above resbiasmin. This gets the device away from any potential marginal performance associated with using the absolute minimum bias. Take a frequency measurement, called freq1a, at this bias, referenced as bias1a.

c. Because resonator frequency is proportional to its thickness, use freq1a to calculate the polysilicon resonator thickness by dividing the frequency by a constant (assume a nominal gap0 such as 800 A, then thickness=freq1a/9018304)

d. Increase the bias by another 100 mV and reference this as bias1b (bias1b=bias1a+0.1). Take a frequency measurement and reference it as freq1b.

e. With freq1a, freq1b, bias1a and bias1b to perform an initial estimate of the gap using two instances of the resonator frequency deviation model (e.g., equation 4), and record or store as gap_a. For example, a subtraction of the two instances of equation 4 cancels out the zero-bias frequency term, thereby yielding a polynomial expression that can be solved for gap size.

The device parameter extraction process continues with the use of gap_a to calculate an initial estimate of the optimal bias via the resonator frequency deviation model (e.g., equation 4) as follows:

a. Determine freq2=freq1a*(1-10 ppm) (Note: about 10 ppm may be useful because, if one selects less than 5 ppm the oscillator may have lower performance, and if one selects larger than 15 ppm the resonator may operate in non-linear mode)

b. Use gap_a, freq1a, bias1a, freq2 to calculate an initial estimate of bias voltage c. Subtract 100 mV safety margin from this value, reference it as bias2a The bias voltage level bias2a is then applied and the output frequency is measured. The frequency is referred to as freq2a. The values for bias2a, freq2a, bias1a, and freq1a are used in Equation 4 to calculate the final gap value, which may then be used with the bias voltage level model (e.g., Equation 5) to calculate the optimal or desired final bias value.

Figure 13:
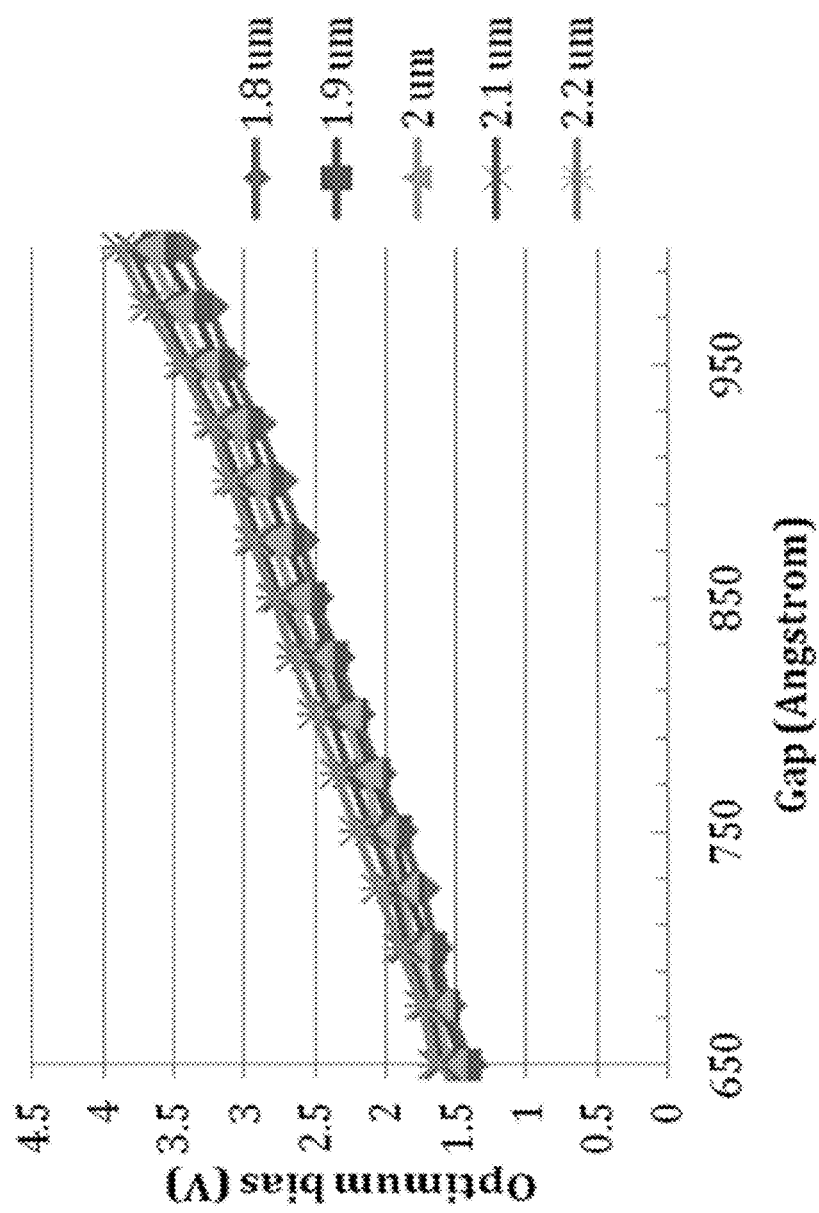
FIG. 13 is a graphical plot depicting a model for optimal bias versus gap for various resonator thicknesses.
Figure 14:
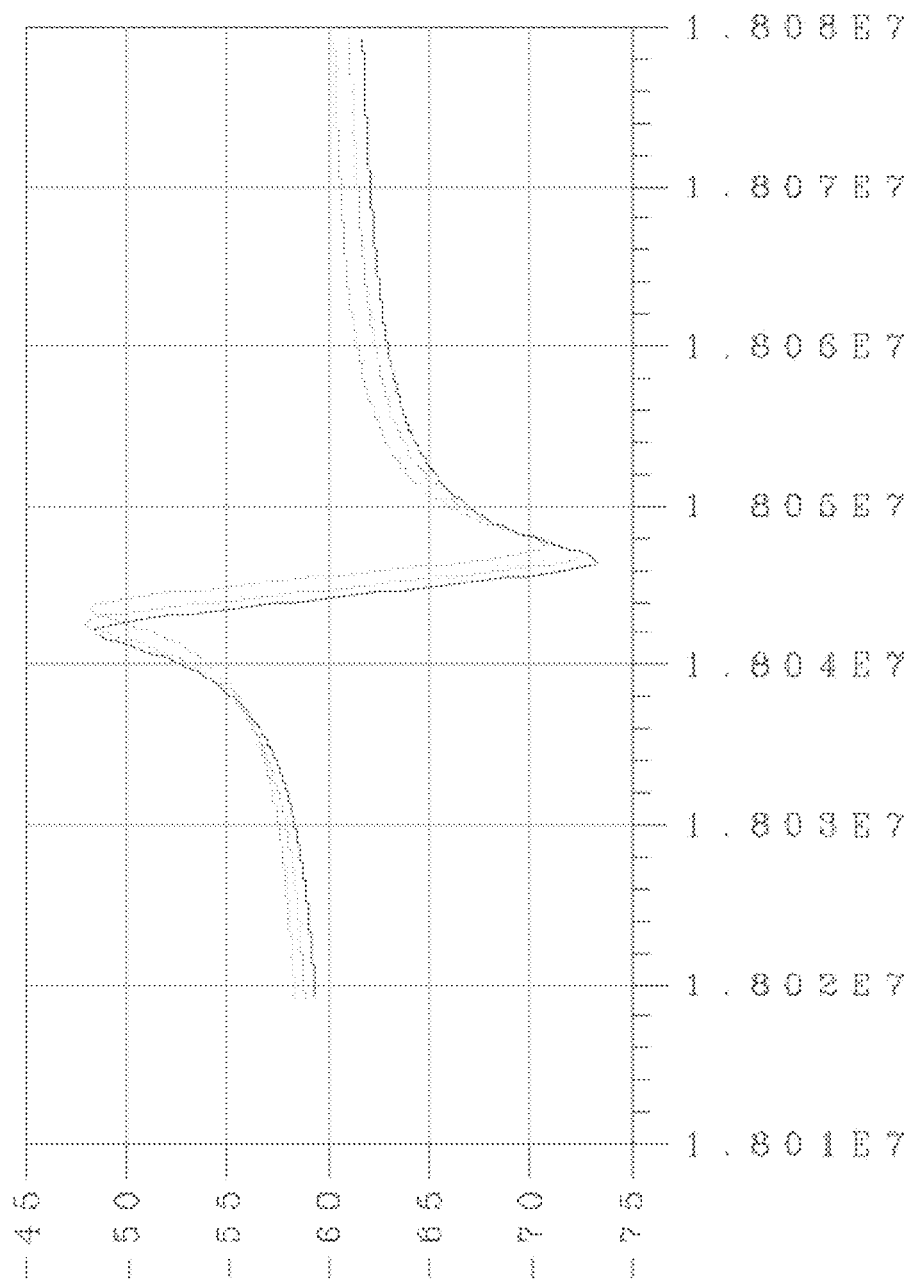
FIGS. 14-16 are graphical plots of simulation results depicting stabilized operation resulting from the implementation and incorporation of the disclosed techniques and device trimming.
Figure 15:
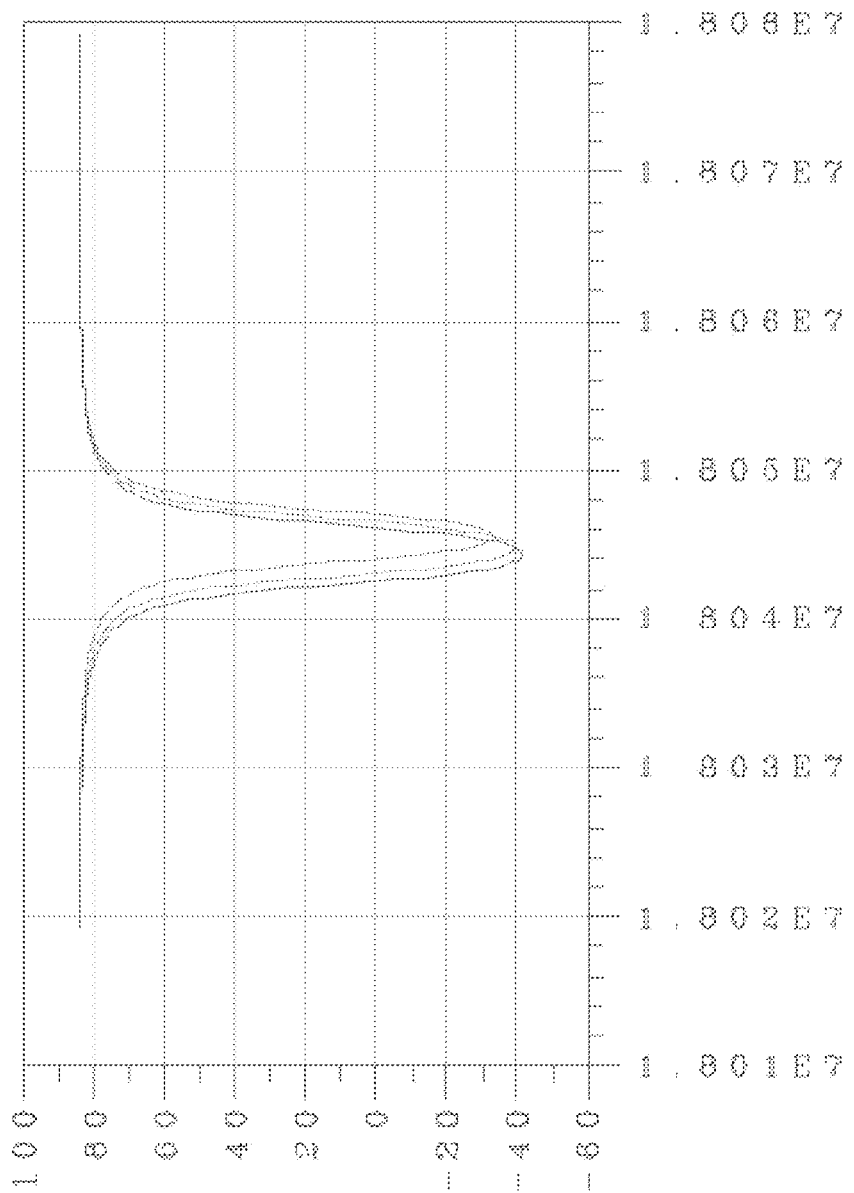
Figure 16:
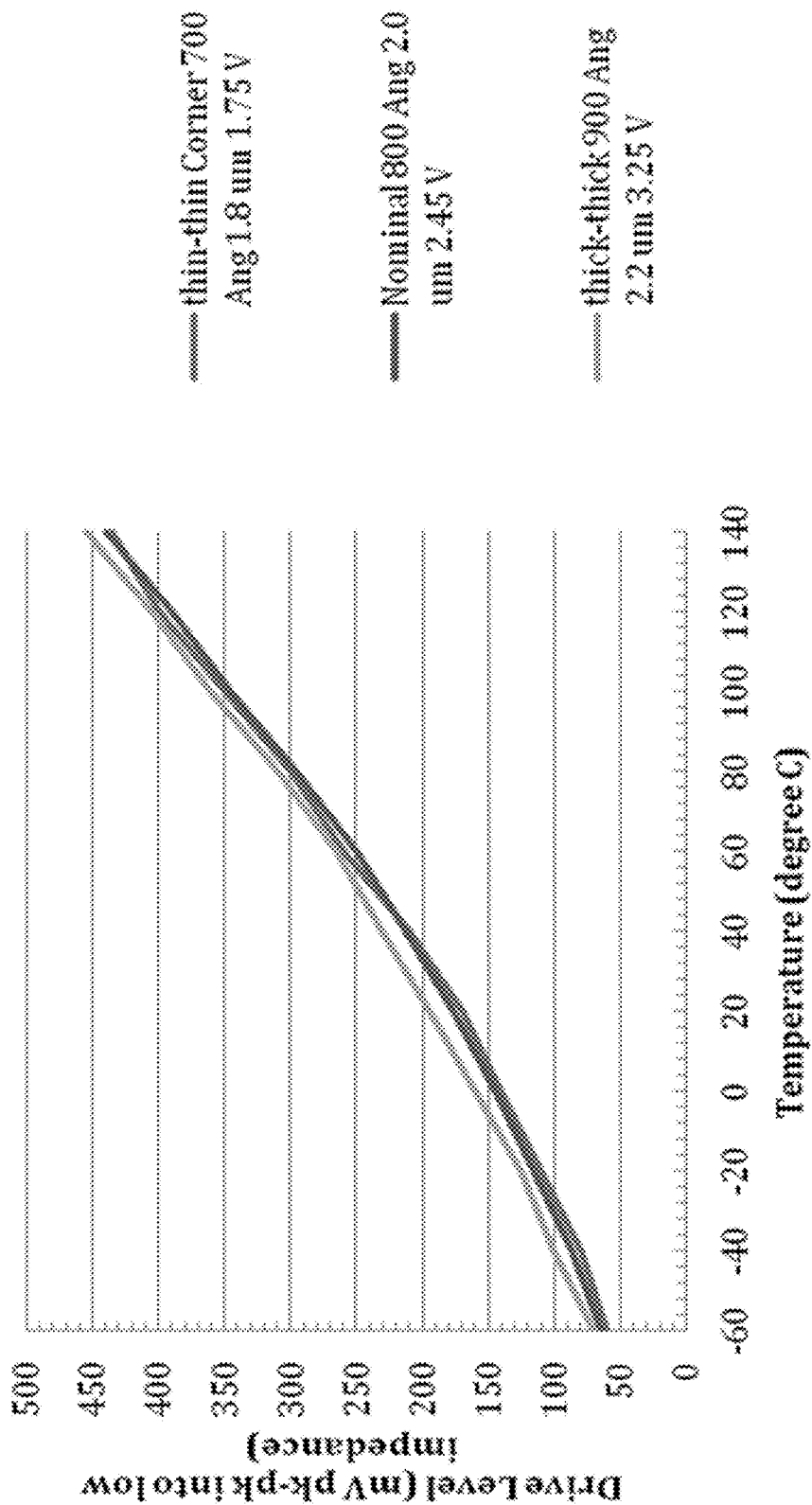

As shown in FIGS. 13-15, simulations using nonlinear modeling show that setting the bias voltage level as described herein stabilizes the device with manufacturing process variations (mainly $d_0$) for small and large signal behavior. FIGS. 13 and 14 depict the small signal amplitude and phase responses for gaps of 700, 800, and 900 Angstrom via tuned bias voltage levels of 1.85 V, 2.45 V, and 3.05 V, respectively. As described above, the disclosed devices may additionally trim the drive or excitation voltage. FIG. 15 depicts the optimal drive level versus temperature for the above gap sizes and trimmed bias voltage levels. With the disclosed trimming methods, the drive level is very consistent across process variations (e.g., gap and thickness) but it still varies with temperature. However, because at low temperatures the noise level of the circuitry is lower, this lower drive level overall does not affect the phase noise performance of the disclosed oscillator devices. The oscillator phase noise remains the same across temperature even when the drive level is different.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding only, and no unnecessary limitations should be understood therefrom, as modifications within the scope of the invention may be apparent to those having ordinary skill in the art.

What is claimed is:

1. A method of configuring a device comprising a microelectromechanical systems (MEMS) resonator, the MEMS resonator comprising a resonant structure to which a bias voltage is applied, the method comprising:
   initiating operation of the device;
   estimating a first parameter of the MEMS resonator based on the initiated operation, the first parameter not varying with the bias voltage;
   monitoring the operation of the device at a plurality of levels of the bias voltage;
   calculating a second parameter of the MEMS resonator based on the monitored operation, the second parameter varying with the bias voltage;
   determining an operational level of the bias voltage based on the estimated first parameter and the calculated second parameter; and
   configuring the device in accordance with the determined operational level of the bias voltage.

2. The method of claim 1, wherein configuring the device comprises storing data indicative of the operational level of the bias voltage in a memory of the device.

3. The method of claim 1, wherein determining the operational level of the bias voltage is further based on a frequency model of the MEMS resonator.

4. The method of claim 3, wherein the frequency model of the MEMS resonator is based on empirical data representative of the operation of the device.

5. The method of claim 1, wherein determining the operational level of the bias voltage comprises estimating the bias voltage that gives rise to an offset in resonant frequency.

6. The method of claim 5, wherein the offset is about 10 parts per million (ppm).

7. The method of claim 1, wherein the first parameter is indicative of a thickness of the resonant structure.

8. The method of claim 1, wherein the second parameter is indicative of a gap between the resonant structure and an electrode to which an excitation voltage is applied.

9. The method of claim 5, wherein the offset is between 5 ppm and 15 ppm.

10. The method of claim 1, wherein initiating the operation comprises determining a minimum level of the bias voltage for oscillation of the MEMS resonator.

11. The method of claim 10, wherein estimating the first parameter comprises measuring a first resonant frequency of the MEMS resonator at a first low level of the plurality of levels of the bias voltage, the first low level being above the minimum level of the bias voltage to ensure a stable start.

12. The method of claim 11, wherein:
   the first parameter is a thickness of the resonant structure; and
   estimating the first parameter further comprises estimating the thickness of the MEMS resonator based on the measured resonant frequency and a predetermined, nominal size of a gap between the resonant structure and an electrode of the MEMS resonator.

13. The method of claim 11, wherein monitoring the operation comprises measuring a second resonant frequency of the MEMS resonator at a second low level of the plurality of levels of the bias voltage differing from the first low level.

14. The method of claim of claim 13, wherein calculating the second parameter comprises estimating a gap between the resonant structure and an electrode of the MEMS resonator based on the first and second resonant frequencies and the first and second low levels of the bias voltage.

15. The method of claim 14, wherein calculating the second parameter further comprises:
   estimating the operational level of the bias voltage based on the estimated gap, a predetermined offset in the resonant frequency, and a frequency model of the MEMS resonator;
   measuring a third frequency of the MEMS resonator at the estimated operational level of the bias voltage; and
   calculating a final value for the gap based on the second low level of the bias voltage, the operational level of the bias voltage, and the second and third resonant frequencies.

16. The method of claim 15, wherein estimating the operational level of the bias voltage comprises lowering the operational level of the bias voltage in accordance with a safety margin.

17. The method of claim 15, wherein calculating the final value comprises subtracting first and second instances of a resonant frequency deviation model from one another to cancel out a zero-frequency term of the resonant frequency deviation model, wherein the first and second instances are based on the second and third resonant frequencies and the second low level of the bias voltage, and the operational level of the bias voltage.

18. The method of claim 13, wherein estimating the gap comprises subtracting first and second instances of a resonant frequency deviation model from one another to cancel out a zero-frequency term of the resonant frequency deviation model, wherein the first and second instances are based on the first and second resonant frequencies and the first and second levels of the bias voltage.

19. The method of claim 1, wherein:
   the first parameter is indicative of a thickness of the resonant structure; and
   the second parameter is indicative of a gap between the resonant structure and an electrode of the MEMS resonator.

20. The method of claim 19, wherein the MEMS resonator is configured such that the resonant frequency is proportional to the thickness of the resonant structure.

\* \* \* \* \*